United States Patent
Kim et al.

(10) Patent No.: US 10,041,098 B2
(45) Date of Patent: Aug. 7, 2018

(54) O-PHOSPHOSERINE EXPORT PROTEIN AND THE METHOD OF PRODUCING O-PHOSPHOSERINE USING THE SAME

(71) Applicant: CJ CHEILJEDANG CORPORATION, Seoul (KR)

(72) Inventors: Hye Won Kim, Gyeonggi-do (KR); Sol Kim, Gyeonggi-do (KR); Jin Sook Chang, Seoul (KR); In Hwa Yoo, Incheon (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 0 days.

(21) Appl. No.: 14/890,423

(22) PCT Filed: May 9, 2014

(86) PCT No.: PCT/KR2014/004161
§ 371 (c)(1),
(2) Date: Nov. 10, 2015

(87) PCT Pub. No.: WO2014/182125
PCT Pub. Date: Nov. 13, 2014

(65) Prior Publication Data
US 2016/0115507 A1    Apr. 28, 2016

(30) Foreign Application Priority Data
May 10, 2013   (KR) .................. 10-2013-0053438

(51) Int. Cl.
*C12P 13/12*   (2006.01)
*C12P 13/06*   (2006.01)
*C07K 14/245*   (2006.01)

(52) U.S. Cl.
CPC ............ *C12P 13/12* (2013.01); *C07K 14/245* (2013.01); *C12P 13/06* (2013.01)

(58) Field of Classification Search
None
See application file for complete search history.

(56) References Cited

U.S. PATENT DOCUMENTS

| | | |
|---|---|---|
| 6,914,131 B1 | 7/2005 | Scarlato et al. |
| 2012/0190081 A1 | 7/2012 | Chang et al. |

FOREIGN PATENT DOCUMENTS

| | | |
|---|---|---|
| EP | 0 885 962 B1 | 4/2005 |
| KR | 10-2012-0041073 A | 4/2012 |
| KR | 10-2012-0041115 | 4/2012 |
| KR | 10-1208267 B1 | 12/2012 |
| WO | WO 2006/089264 A2 | 8/2006 |
| WO | WO 2013/096475 A1 | 6/2013 |

OTHER PUBLICATIONS

Blattner et al., "The Complete Genome Sequence of *Escherichia coli* K-12", Science, 1997, 277:1453-1462 and Supplemental Information, pp. 1-6.*
Lin et al., "MacB ABC Transporter Is a Dimer Whose ATPase Activity and Macrolide-binding Capacity Are Regulated by the Membrane Fusion Protein MacA", The Journal of Biological Chemistry, 2009, vol. 284, No. 2, pp. 1145-1154; and Supplemental Data, pp. 1-12.*
GenBank: U000096.2, "*Escherichia coli* str. K-12 substr. MG1655, complete genome," Feb. 26, 2013, 2 pages.
Franke et al., "YfiK from *Escherichia coli* Promotes Export of O-Acetylserine and Cysteine," J. Bacteriol. 185(4): 1161-1166, Feb. 2003.
Kobayashi et al., "Novel Macrolide-Specific ABC-Type Efflux Transporter in *Escherichia coli*," J. Bacteriology 183 (19): 5639-5644, Oct. 2001.
Korean Intellectual Property Office, International Search Report for International Application No. PCT/KR2014/004161, dated Sep. 22, 2014, four pages.
NCBI Reference Sequence: NP_415400.1, "fused macrolide transporter subunits of ABC superfamily: ATP-binding component/membrane component [*Escherichia coli* str. K-12 substr. MG1655]," accessed Mar. 4, 2013.
NCBI Reference Sequence: WP_001466488.1, "homoserine/homoserine lactone efflux protein [*Escherichia coli*]," accessed May 3, 2013.
NCBI Reference Sequence: ZP_07143650.1, "YGGT family protein [*Escherichia coli* MS 187-1]," accessed Nov. 27, 2012.
Ryu et al., "Continuous L-Cysteine production using immobilized cell reactors and product extractors," Process Biochemistry 32(3): 201-209, 1997.
Wada and Takagi, "Metabolic pathways and biotechnological production of L-Cysteine," Appl. Microbiol. Biotechnol. 73:48-54, 2006.
Westrop et al., "Cysteine biosynthesis in Trichomonas vaginalis involves cysteine synthase utilizing O-phosphoserine," J. Biol. Chem. 281(35): 25062-25075, Sep. 1, 2006.
Zakataeva et al., "The novel transmembrane *Escherichia coli* proteins involved in the amino acid reflux," FEBS Letters 452: 228-232, 1999.

* cited by examiner

*Primary Examiner* — Suzanne M Noakes
(74) *Attorney, Agent, or Firm* — Cooley LLP (57) ABSTRACT

The present invention relates to a novel isolated polypeptide having the ability to export O-phosphoserine (OPS) that is a precursor of L-cysteine, a vector comprising the polynucleotide, an OPS-producing microorganism having enhanced activity of the polypeptide, a method of producing OPS using the microorganism, and a method for preparing cysteine or its derivatives, which comprises reacting OPS, produced by the above method, with a sulfide in the presence of O-phosphoserine sulfhydrylase (OPSS) or a microorganism that expresses OPSS.

8 Claims, 2 Drawing Sheets

O-PHOSPHOSERINE EXPORT PROTEIN AND THE METHOD OF PRODUCING O-PHOSPHOSERINE USING THE SAME

CROSS-REFERENCES TO RELATED APPLICATIONS

This application is a U.S. national phase application of International PCT Patent Application No. PCT/KR2014/004161, which was filed on May 9, 2014, which claims priority to Korean Patent Application Nos. 10-2013-0053438, filed May 10, 2013. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_039_01US_SeqList_ST25.txt. The text file is 15 KB, was created on Nov. 10, 2015, and is being submitted electronically via EFS-Web.

BACKGROUND OF THE INVENTION

Field of the Invention

The present invention relates to a novel isolated polypeptide having the ability to export O-phosphoserine (hereinafter described as "OPS") that is a precursor of L-cysteine, a polynucleotide encoding the polypeptide, a vector comprising the polynucleotide, an OPS-producing microorganism having enhanced activity of the polypeptide, a method of producing OPS using the microorganism, and a method for preparing cysteine or its derivatives, which comprises reacting OPS produced by the above OPS-producing method with a sulfide in the presence of O-phosphoserine sulfhydrylase (OPSS) or a microorganism that expresses OPSS.

Description of the Prior Art

L-cysteine, an amino acid playing an important role in the metabolism of sulfur in all living organisms, is used not only in the synthesis of biological proteins such as hair keratin, glutathione, biotin, methionine, and other sulfur-containing metabolites, but also as a precursor for biosynthesis of coenzyme A.

Known methods of producing L-cysteine using microorganisms include a method of biologically converting D,L-ATC to L-cysteine using microorganisms (Ryu O H et al., Process Biochem., 32:201-209, 1997). Another known method is a method of producing L-cysteine by direct fermentation using *E. coli* (EP 0885962B; Wada M and Takagi H, Appl. Microbiol. Biochem., 73:48-54, 2006). Meanwhile, the present inventors conducted studies to develop a new method for producing L-cysteine, and as a result, found an enzyme (O-phosphoserine sulfhydrylase (OPSS)) that synthesizes L-cysteine from O-phosphoserine (OPS) in certain microorganisms. Based on this finding, the present inventors developed a method of producing cysteine by reacting OPS with the OPSS enzyme by culturing a mutated microorganism to accumulate OPS therein (Korean Patent Publication No. 10-2012-004111). The needs still exist to produce OPS in excessive amounts in order to produce cysteine at high yield. Accordingly, the present inventors have made extensive efforts to discover an appropriate exporter that enables O-phosphoserine produced in an OPS-producing strain to be released from cells smoothly. In addition, based on various kinds of known transporters, the present inventors screened ydeD encoding O-acetylserine/cysteine efflux pump protein, yfiK encoding O-acetylserine/cysteine efflux permease (Franke I, Resch A, Dassler T, Maier T and Bock A, J. Bacteriology, 185: 1161-166, 2003), rhtB encoding homoserine/homoserine lactone efflux pump protein (Zakataeva N P, Aleshin V V, Tokmakova I L, Troshin P V, Livshits V A FEBS Lett 1999:452(3); 228-32) and the like, and particularly found that the enhancement of RhtB in the OPS-producing strain results in an increase in the concentration of OPS (Korean Patent Publication No. 10-2012-0041115). However, for the production of higher yield of cysteine, the development of a transporter having a higher ability to export OPS is still required.

SUMMARY OF THE INVENTION

The present inventors have made extensive efforts to discover proteins having OPS exporting activity so as to be able to further increase the production of OPS, and as a result, have identified two novel polypeptides having excellent OPS exporting activity and have found that the polypeptides can export OPS from an OPS-producing strain more effectively, thereby completing the present invention.

It is an object of the present invention to provide a method for producing O-phosphoserine (OPS), comprising culturing an O-phosphoserine-producing microorganism having enhanced activity of a polypeptide which has an amino acid sequence of SEQ ID NO: 1 or 2 and has OPS exporting activity.

Another object of the present invention is to provide a novel isolated polypeptide having an amino acid sequence of SEQ ID NO: 1 or 2, which has O-phosphoserine exporting activity.

Still another object of the present invention is to provide a polynucleotide encoding the polypeptide and a vector comprising the polynucleotide.

Still another object of the present invention is to provide an O-phosphoserine-producing microorganism having enhanced activity of a polypeptide which has an amino acid sequence of SEQ ID NO: 1 or 2 and has O-phosphoserine (OPS) exporting activity.

Still another object of the present invention is to provide a method for producing cysteine or its derivatives, comprising reacting O-phosphoserine, produced by the above-described method for producing O-phosphoserine, with a sulfide in the presence of O-phosphoserine sulfhydrylase (OPSS) or a microorganism that expresses OPSS.

DETAILED DESCRIPTION OF THE INVENTION

Aspect of the present invention includes a method for producing O-phosphoserine (OPS), comprising culturing an O-phosphoserine-producing microorganism having enhanced activity of a polypeptide which has an amino acid sequence of SEQ ID NO: 1 or 2 and has O-phosphoserine (OPS) exporting activity.

Specifically, the method according to above aspect of the present invention may comprise the steps of: a) producing OPS by culturing an OPS-producing microorganism having enhanced activity of a polypeptide which has an amino acid sequence of SEQ ID NO: 1 or 2 and has OPS exporting activity; and b) isolating OPS from the culture of the microorganism, but is not limited thereto.

Step a) of the method of the present invention is a step of culturing an OPS-producing microorganism having enhanced activity of a polypeptide which has an amino acid sequence of SEQ ID NO: 1 or 2 and has OPS exporting activity.

As used herein, the term "O-phosphoserine (hereinafter described as "OPS")" refers to an ester of serine and phosphoric acid that is a component of many proteins. The OPS is a precursor of L-cysteine and can be converted to cysteine by reaction with a sulfide under the catalytic action of OPS sulfhydrylase (hereinafter described as "OPSS"). Accordingly, it is an important factor to increasing productivity of OPS in the production of cysteine, and thus it has been required to develop transporters that enable intracellular OPS to be effectively secreted from OPS-producing strains.

As used herein, the expression "polypeptide having O-phosphoserine (OPS) exporting activity" refers to a membrane protein having OPS exporting activity. Specifically, the polypeptide is an *E. coli* membrane protein. The present inventors have identified two *E. coli* membrane proteins that are novel membrane proteins capable of exporting OPS from cells and derived from *E. coli* which could grow under the condition in which an excessive amount of OPS is present. Specifically, the novel *E. coli* membrane proteins having OPS exporting ability is identified YggT having an amino acid sequence of SEQ ID NO: 1, which is a predicted inner membrane protein, and MacB (MacAB-TolC macrolide export transport system-membrane subunit) having an amino acid sequence of SEQ ID NO: 2. It is known that the YggT protein of SEQ ID NO: 1 acts as an *E. coli* inner membrane protein and the MacB protein of SEQ ID NO: 2 functions as a macrolide transporter, but the OPS exporting activity of the proteins was not known prior to the present invention and was first identified by the present inventors. In addition, the scope of the polypeptide of the present invention encompasses, not only the polypeptide having the amino acid sequence of SEQ ID NO: 1 or 2, but also a membrane protein that has an amino acid sequence having a homology of at least 70%, specifically at least 80%, more specifically at least 90%, even more specifically at least 95%, even more specifically at least 98%, and most specifically at least 99%, with the amino acid sequence of SEQ ID NO: 1 or 2, and substantially has OPS exporting activity that is identical or comparable to that of the polypeptide of SEQ ID NO: 1 or 2. In addition, it is obvious that a polypeptide variant comprising a deletion, modification, substitution or addition in one or more amino acid residues of the amino acid sequence of SEQ ID NO: 1 or 2 falls within the scope of the present invention, as long as it has the above-described homology and substantially has OPS exporting activity.

As used herein, the term "homology" refers to the percentage of identity between two polynucleotide or polypeptide moieties. The correspondence between the sequences from one form to another can be determined by techniques known in the art. For example, homology can be determined by a direct comparison of the sequence information between two polypeptide molecules by aligning the sequence information and using readily available computer programs. Alternatively, homology can be determined by hybridization of polynucleotides under conditions which form stable duplexes between homologous regions, followed by digestion with single-stranded-specific nuclease, and size determination of the digested fragments.

As used herein, the term "homologous" in all its grammatical forms and spelling variations refers to the relationship between proteins that possess a "common evolutionary origin," including proteins from superfamilies and homologous proteins from different species. Such proteins (and their encoding genes) have sequence homology, as reflected by their high degree of sequence similarity. However, in common usage and in the present invention, the term "homologous," when modified with an adjective such as "very high," may refer to sequence similarity and not a common evolutionary origin.

As used herein, the term "sequence similarity" refers to the degree of identity or correspondence between nucleic acid or amino acid sequences of proteins that may or may not share a common evolutionary origin. In one embodiment, two amino acid sequences are "substantially homologous" or "substantially similar" when at least about 21% (specifically at least about 50%, and most specifically at least about 75%, 90%, 95%, 96%, 97% or 99%) of the polypeptide match over the defined length of the amino acid sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art (see, e.g., Sambrook et al., 1989, infra).

In an example of the present invention, it was shown that a strain with an enhanced activity of the polypeptide having the amino acid sequence of SEQ ID NO: 1 or an enhanced activity of the polypeptide having the amino acid sequence of SEQ ID NO: 2 has excellent OPS secreting activity compared to a strain having enhanced rhtB, emrD or ycaD, which is a comparative group (Example 3).

As described above, the polypeptide of the present invention has excellent OPS exporting activity, and thus when a microorganism having enhanced activity of the polypeptide is cultured, OPS can be effectively produced.

A method for enhancing the activity of the polypeptide is not specifically limited, as long as it can enhance the activity of the polypeptide. Examples of this method include a method of increasing the intracellular copy number of a gene encoding the polypeptide, a method of introducing a mutation into an expression regulatory sequence for the chromosomal gene encoding the polypeptide, a method of replacing an expression regulatory sequence for the chromosomal gene encoding the polypeptide with a sequence having strong activity, a method of substituting the chromosomal gene encoding the polypeptide with a gene mutated to increase the activity of the polypeptide, and a method of introducing a mutation into the chromosomal gene encoding the polypeptide to enhance the activity of the polypeptide. The method of enhancing the activity of the polypeptide can likewise be applied to enhance the activities of other polypeptides. In an example of the present invention, which show a typical method capable of enhancing the activity of the polypeptide, the activity of the inventive polypeptide having the amino acid sequence of SEQ ID NO: 1 or SEQ ID NO: 2 was enhanced by introducing a vector, which comprises a polynucleotide encoding the polypeptide, into an OPS-producing microorganism.

As used herein, the term "introduction" refers to a method of transferring a vector, which comprises a polynucleotide encoding the polypeptide, to a host cell. This introduction may be easily performed using any conventional method known in the art. In general, examples of the introduction method include $CaCl_2$ precipitation, the Hanahan method that is an improved $CaCl_2$ method that uses DMSO (dimethyl sulfoxide) as a reducing material to increase efficiency, electroporation, calcium phosphate precipitation, protoplast fusion, agitation using silicon carbide fiber, *Agrobacterium*-mediated transformation, PEG-mediated transformation, dextran sulfate-mediated transformation, lipofectamine-mediated transformation, and desiccation/inhibition-mediated transformation. The method for transforming a vector that comprises a polynucleotide encoding the polypeptide of the present invention is not limited to the above-described examples, and any conventional transformation or transfection methods known in the art may be used without limitation.

As used herein, the term "OPS-producing microorganism" refers to a prokaryotic or eukaryotic microbial strain capable of producing OPS therein, specifically a microorganism capable of accumulating OPS therein by genetic engineering. For the purpose of the present invention, the microorganism may be any prokaryotic or eukaryotic microorganism that has enhanced activity of the polypeptide the polypeptide of SEQ ID NO: 1 or 2, and thus can produce OPS. Examples of the microorganism include microbial strains belonging to the genus *Escherichia*, the genus *Erwinia*, the genus *Serratia*, the genus *Providencia*, the genus *Corynebacterium* and the genus *Brevibacterium*. Specifically, the microorganism may be a microorganism of the genus *Escherichia*. More specifically, it may be *E. coli*. Particularly, a microorganism of the *Escherichia* or the genus *Corynebacterium* can produce OPS and L-serine, because it contains SerA, SerC and SerB proteins that are enzymes in the biosynthesis pathway of L-serine (Ahmed Zahoor, Computational and structural biotechnology journal, vol 3, 2012 october; Wendisch V F et al., Curr Opin Microbiol. 2006 June; 9(3):268-74; Peters-Wendisch P et al., Appl Environ Microbiol. 2005 November; 71(11):7139-44). In an example of the present invention, *E. coli* was used as a representative example of the OPS-producing microorganism.

Further, the OPS-producing microorganism may further be a microorganisms modified to reduce the activity of endogenous phosphoserine phosphatase (hereinafter described as "SerB").

The SerB has an activity of converting OPS to L-serine, and thus the microorganism modified to reduce the SerB activity has the property of accumulating OPS therein, suggesting that it is useful for the production of OPS. The reduction in the activity of SerB means that the activity of SerB is reduced compared to that in a non-mutated strain or is removed. The reduction in the activity of SerB can be achieved using various methods well known in the art. Examples of the method for reducing the activity of the SerB enzyme include, but are not limited to, a method of substituting the chromosomal gene encoding the enzyme with a gene mutated to reduce or remove the activity of the enzyme, a method of introducing a mutation into an expression regulatory sequence for the chromosomal gene encoding the enzyme, a method of replacing an expression regulatory sequence for the chromosomal gene encoding the enzyme with a gene having weak activity, deleting the chromosomal gene encoding the enzyme, a method of introducing an antisense oligonucleotide that binds complementarily to the transcript of the chromosomal gene to inhibit the translation of the mRNA into the protein, a method of artificially adding a sequence complementary to the SD sequence of the gene encoding the enzyme in the front of the SD sequence to form a secondary structure that makes the adhesion of ribosome impossible, and a reverse transcription engineering (RTE) method of adding a promoter to the 3' end of the open reading frame (ORF) of the corresponding sequence so as to be reverse-transcribed. In an example of the present invention, a vector comprising a polynucleotide encoding the inventive polypeptide of SEQ ID NO: 1 or 2 was introduced into the microorganism, CA07-0012 (accession number: KCCM11121P) disclosed in Korean Patent Publication No. 10-2012-004115 and US Patent Laid-Open Publication No. 2012-0190081, as a microorganism mutated to reduce the activity of endogenous SerB.

Further, the OPS-producing microorganism may be a microorganism having enhanced activity of phosphoglycerate dehydrogenase (hereinafter described as "SerA") or phosphoserine aminotransferase (hereinafter described as "SerC").

The SerA is a protein having an activity of converting 3-phosphoglycerate to 3-phosphohydroxypyruvate, and the SerA may be a wild-type protein or a variant resistant to serine feedback inhibition. Also, the SerC is a protein having an activity of converting 3-phosphoglycerate to O-phosphoserine. Thus, the microorganism with enhanced activity of SerA and/or SerC may be useful as an OPS-producing strain. In an example of the present invention, using CA07-0022/pCL-Prmf-serA*(G336V)-serf (accession number: KCCM11103P), which is a microorganism having enhanced activity of SerA (resistant to serine feedback inhibition) and SerC as disclosed in Korean Patent Publication No. 10-2012-004115, as the OPS-producing microorganism, an expression vector encoding the polypeptide of SEQ ID NO: 1 or 2 was introduced into the microorganism to produce OPS. Also, CA07-0022/pCL-Prmf-serA*(G336V)-serC-PrhtB-yggT, which is a representative strain having enhanced activity of yggT of SEQ ID NO: 1, is a microbial strain having enhanced activities of SerC and SerA resistant to serine feedback inhibition and has the yggT protein gene of SEQ ID NO: 1 introduced therein. This CA07-0022/pCL-Prmf-serA*(G336V)-serC-PrhtB-yggT was named "*Escherichia coli* CA07-0228" and deposited with the Korean Culture Center of Microorganisms, recognized as an international depositary authority under the Budapest Treaty, on Mar. 7, 2013 under the accession number KCCM11399P. In addition, CA07-0022/pCL-Prmf-serA*(G336V)-serC-PrhtB-macB, which is a representative strain having enhanced activity of MacB of SEQ ID NO: 2, is a microbial strain having enhanced activities of SerC and SerA resistant to serine feedback inhibition and has the MacB protein gene of SEQ ID NO: 2 introduced therein. This CA07-0022/pCL-Prmf-serA*(G336V)-serC-PrhtB-macB was named "*Escherichia coli* CA07-0229" and deposited with the Korean Culture Center of Microorganisms, recognized as an international depositary authority under the Budapest Treaty, on Mar. 7, 2013 under the accession number KCCM11400P (Example 2).

In addition, the microorganism may further have a reduced ability to perform the intracellular uptake or degradation of OPS. Specifically, the microorganism may be a microorganism mutated to reduce the activity of PhnC/

PhnD/PhnE alkylphosphonate ABC transporter (PhnCDE operon, that is, ATP-binding component of phosphonate transport (PhnC; EG 10713)-periplasmic binding protein component of Pn transporter (PhnD; EG 10714)-integral membrane component of the alkylphosphonate ABC transporter (PhnE; EG 11283)), alkaline phosphatase (PhoA) or acid phosphatase (AphA).

In addition, the microorganism of the present invention may further have enhanced activity of pyrimidine nucleotide transhydrogenase (PntAB; EC 1.6.1.1). As previously described in Sauer U P et al., J Biol Chem. 20; 279(8):6613-9. Epub 2003, PntAB participates in the metabolism of NADPH to regulate the intracellular redox balance.

As used herein, the term "culturing" means growing the microorganism under artificially controlled conditions. A culturing process in the present invention may be performed using a suitable medium and culture conditions well known in the art. Any person skilled in the art can readily control the culture process depending on the type of strain selected. Specifically, the culturing may be batch-type culture, continuous culture or fed-batch culture, but is not limited thereto.

In culture of the recombinant microorganism having reduced activity of endogenous SerB, the medium should additionally contain glycine or serine, because the serine auxotrophy of the recombinant microorganism is induced. Glycine may be provided in the form of purified glycine, a glycine-containing yeast extract, or tryptone. The concentration of glycine in the medium is generally 0.1-10 g/L, and specifically 0.5-3 g/L. In addition, serine may be provided in the form of purified serine, a serine-containing yeast extract or tryptone. The concentration of serine in the medium is generally 0.1-5 g/L, and specifically 0.1-1 g/L.

In addition, the medium contains a carbon source. Examples of the carbon source include saccharides and carbohydrates such as glucose, sucrose, lactose, fructose, maltose, starch and cellulose, oils and fats such as soybean oil, sunflower oil, castor oil and coconut oil, fatty acids such as palmitic acid, stearic acid and linoleic acid, alcohols such as glycerol and ethanol, and organic acids such as acetic acid. These carbon sources may be used alone or in combination in the medium. Examples of a nitrogen source that may be contained in the medium include organic nitrogen sources such as peptone, yeast extract, meat juice, malt extract, corn steep liquor, soybean, and wheat protein, and inorganic nitrogen sources such as urea, ammonium sulfate, ammonium chloride, ammonium phosphate, ammonium carbonate and ammonium nitrate. These nitrogen sources may be used alone or in combination. Examples of a phosphorous source that may be contained in the medium include potassium dihydrogen phosphate, potassium phosphate, and corresponding sodium salts. In addition, the medium may contain metal salts such as magnesium sulfate or iron sulfate. Additionally, the medium may also contain amino acids, vitamins and suitable precursors. These sources or precursors may be added to the medium in a batch or continuous manner.

Compounds such as ammonium hydroxide, potassium hydroxide, ammonia, phosphoric acid and sulfuric acid may be added to the medium in a suitable manner during culturing to adjust the pH of the culture medium. In addition, during culturing, a defoaming agent such as fatty acid polyglycol ester may be used to suppress the formation of foam. Further, in order to maintain the culture medium in an aerobic state, oxygen or oxygen-containing gas can be injected into the culture medium. For an anaerobic or microaerobic condition, nitrogen, hydrogen, or carbon dioxide may be provided without aeration. The culture medium is typically maintained at a temperature ranging from 27° C. to 37° C., and specifically from 30° C. to 35° C. As for the culture period, culture can be continued until desired amounts of useful substances are produced. Specifically, the culture period is 10-100 hours.

Step b) of the method of the present invention is a step of isolating the produced OPS.

In the present invention, the OPS produced in the culturing step may further be isolated and purified. For example, the desired OPS can be collected from the culture using a suitable method known in the art depending on a culture method, for example, a batch-type culture, continuous culture or fed-batch culture method.

Figure 1:
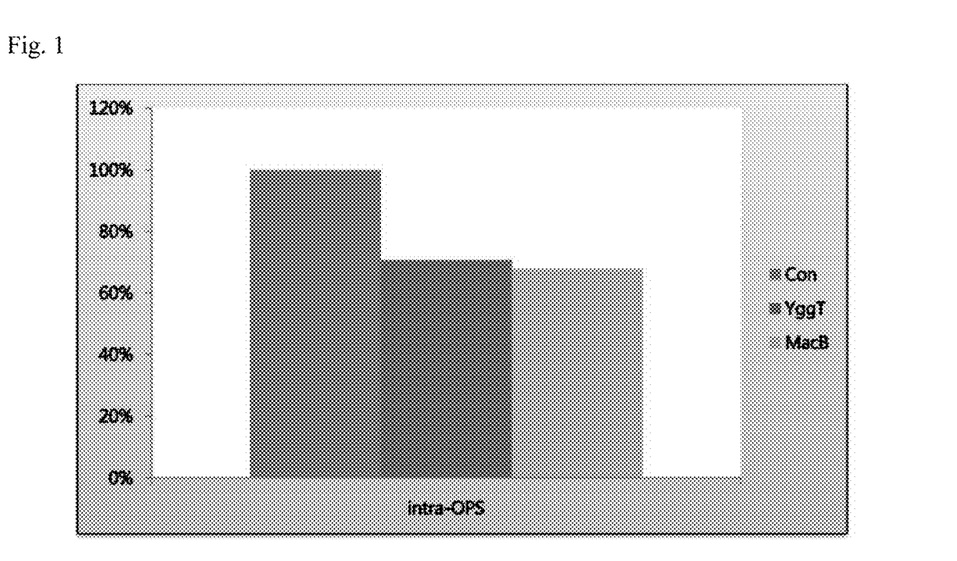
FIG. 1 is a graphic diagram showing the results of measuring intracellular OPS by high-performance liquid chromatography (HPLC) after completely removing OPS released from a culture of the inventive recombinant microorganism having enhanced activities of YggT and MacB proteins.
Figure 2:
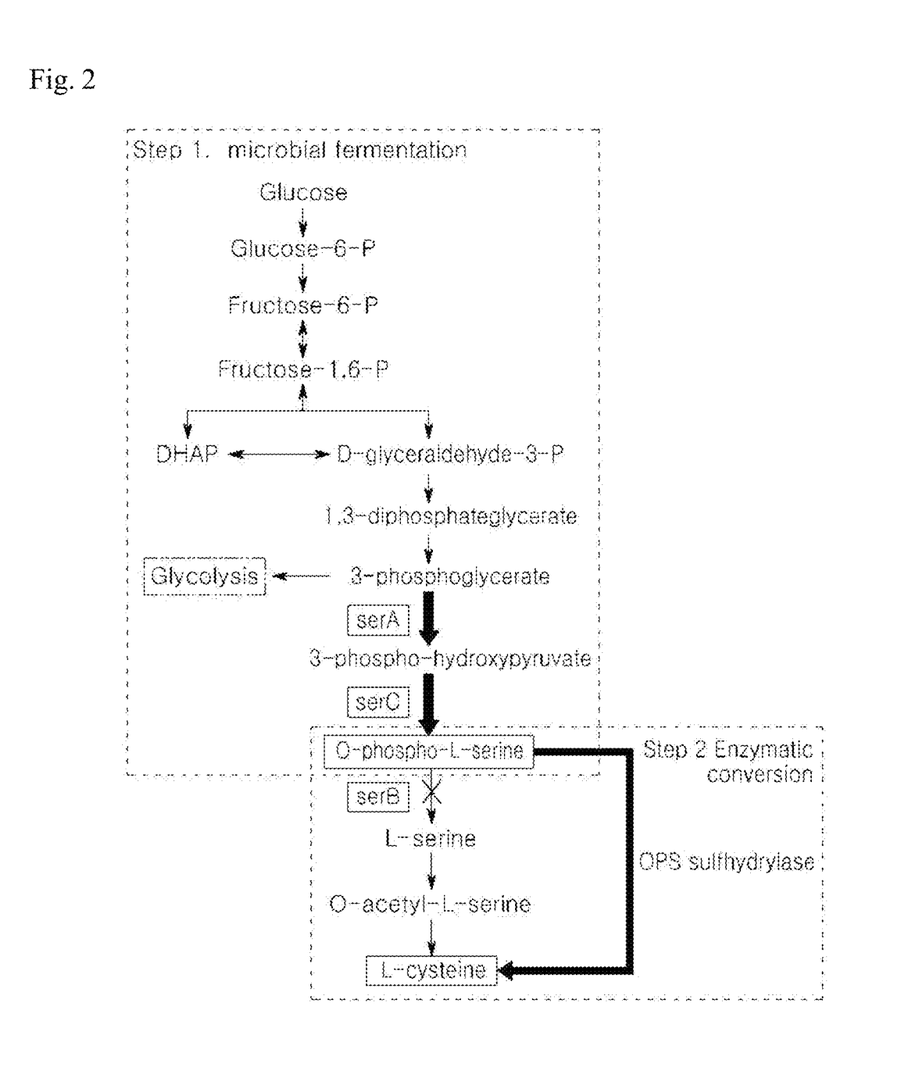
FIG. 2 is a schematic diagram showing a method of producing L-cysteine by accumulating O-phosphoserine from the biosynthesis and microbial fermentation of O-phosphoserine and enzymatically converting the accumulated O-phosphoserine to L-cysteine.

In an example of the present invention, a novel polypeptide having OPS exporting activity, which is defined by the amino acid sequence of SEQ ID NO: 1 or 2, was identified (Example 1). Also, the productivity of OPS was examined typically in CA07-0012 that is an OPS-producing strain having reduced activity of SerB together with RhtB protein known to have OPS exporting activity, the $E.$ $coli$ membrane protein EmrD belonging to the major facilitator superfamily (MFS) to which MacB of the present invention, and YcaD MFS transporter. As a result, it was shown that, compared to the control CA07-0012 showing an OPS productivity of 1.1 g/L, an OPS-producing strain that expresses the inventive polypeptide defined by SEQ ID NO: 1 showed an OPS productivity of 1.6 g/L, and an OPS-producing strain that expresses the inventive polypeptide defined by SEQ ID NO: 2 showed an OPS productivity of 1.5 g/L. Also, an OPS-producing strain as a comparative group expressing RhtB showed an OPS productivity of 1.3 g/L, which was lower than that of the OPS-producing strain expressing the inventive peptide, and OPS-producing strains expressing EmrD and YacD showed OPS productivities of 1.2 g/L and 0.9 g/L, respectively, which were equal to or lower than that of the control group (Table 3 and Example 3). In addition, the above results were verified using the OPS-producing strain CA07-0022/pCL-Prmf-serA*(G336V)-serC having enhanced activities of SerA and SerC that are involved in the biosynthesis pathway of OPS, and as a result, it was confirmed that the OPS-producing strain expressing the polypeptide of the present invention showed high OPS productivity compared to those of the control group and the comparative group that expresses EmrD or YcaD (Table 4 and Example 3). In addition, in the present invention, in order to confirm whether the polypeptide of the present invention shows an OPS export function, exported OPS was removed from the medium in which a strain having enhanced activities of YggT and MacB proteins was cultured, after which the intracellular concentration of OPS was measured. As a result, it was shown that the strain having enhanced YggT and MacB activities showed a decrease in OPS concentration of about 30% compared to the control group, suggesting that the polypeptide of the present invention functions as an OPS export function (FIG. 1 and Example 4).

A further aspect of the present invention also includes an isolated polypeptide having O-phosphoserine (OPS) exporting activity, which is defined by the amino acid sequence of SEQ ID NO: 1 or SEQ ID NO: 2, a polynucleotide encoding the polypeptide, and a vector comprising the polynucleotide.

Herein, the O-phosphoserine and the polypeptide are described above.

As used herein, the term "polynucleotide" refers to a polymer of nucleotide units linked to each other by a covalent bond to form a chain. It generally means a DNA or RNA strand having any length.

A polynucleotide encoding the inventive polypeptide having the amino acid sequence of SEQ ID NO: 1 may specifically be a polynucleotide having a polynucleotide sequence of SEQ ID NO: 3, but is not limited thereto. In addition, the scope of the polypeptide of the present invention may encompasse, not only the polynucleotide having the polynucleotide sequence of SEQ ID NO: 3, but also a polynucleotide that has a nucleotide sequence having a similarity of at least 70%, specifically at least 80%, more specifically at least 90%, even more specifically at least 90%, even more specifically at least 95%, and most specifically at least 98%, to the polynucleotide sequence of SEQ ID NO: 3, and can encode a polypeptide substantially having OPS exporting activity. Further, it is obvious that a variant having an polynucleotide sequence comprising a deletion, modification, substitution or addition in at least one amino acid residues also falls within the scope of the present invention.

Moreover, a polynucleotide encoding the inventive polypeptide having the amino acid sequence of SEQ ID NO: 2 may specifically be a polynucleotide having a polynucleotide sequence of SEQ ID NO: 4, but is not limited thereto. In addition, the scope of the present invention may encompasse, not only the polynucleotide having the polynucleotide sequence of SEQ ID NO: 4, but also a polynucleotide that has a nucleotide sequence having a similarity of at least 70%, specifically at least 80%, more specifically at least 90%, even more specifically at least 90%, even more specifically at least 95%, and most specifically at least 98%, to the polynucleotide sequence of SEQ ID NO: 4, and can encode a polypeptide substantially having OPS exporting activity. Further, it is obvious that a variant having an polynucleotide comprising a deletion, modification, substitution or addition in at least one amino acid residues also falls within the scope of the present invention.

As used herein, the term "vector" refers to any vehicle for the cloning of and/or transfer of a nucleic acid into a host cell. A vector may be a replicon to which another DNA segment may be attached so as to bring about the replication of the attached segment. A "replicon" refers to any genetic element (e.g., plasmid, phage, cosmid, chromosome, virus) that functions as an autonomous unit of DNA replication in vivo, i.e., capable of replication under its own control. The term "vector" may include both viral and nonviral vehicles for introducing the nucleic acid into a host cell in vitro, ex vivo or in vivo. The term "vector" may also include minicircle DNAs. For example, the vector may be a plasmid without bacterial DNA sequences. The removal of bacterial DNA sequences which are rich in CpG regions has been shown to decrease transgene expression silencing and result in more persistent expression from plasmid DNA vectors (e.g., Ehrhardt, A. et al. (2003) HumGene Ther 10: 215-25; Yet, N. S. (2002) Mol Ther 5: 731-38; Chen, Z. Y. et al. (2004) Gene Ther 11: 856-64). The term "vector" may also include transposons (Annu Rev Genet. 2003; 37:3-29), or artificial chromosomes. Specifically, the vector that is used in the present invention may be a pACYC177, pACYC184, pCL1920, pECCG117, pUC19, pBR322 or pMW118 vector. In an example of the present invention, a pCL1920 vector was used.

A further aspect of the present invention also includes an O-phosphoserine-producing microorganism having enhanced activity of a polypeptide that has an amino acid sequence of SEQ ID NO: 1 or 2 and that has O-phosphoserine exporting activity.

Herein, the O-phosphoserine, the polypeptide and the O-phosphoserine-producing microorganism are as described above.

A further aspect of the present invention also includes a method for producing cysteine or its derivatives, the method comprising reacting O-phosphoserine, produced by the above-described method for producing O-phosphoserine, with a sulfide in the presence of O-phosphoserine sulfhydrylase (OPSS) or a microorganism that expresses OPSS.

Specifically, the method for producing cysteine or its derivatives comprises the steps of: a) producing OPS by culturing an OPS-producing microorganism having enhanced activity of a polypeptide that has an amino acid sequence of SEQ ID NO: 1 or 2 and has OPS exporting activity; and b) reacting the OPS, produced in step a), with a sulfide in the presence of O-phosphoserine sulfhydrylase (OPSS) or a microorganism that expresses OPSS.

As used herein, the term "O-phosphoserine sulfhydrylase (described as "OPSS")" refers to an enzyme that catalyzes a reaction in which a thiol (SH) group is provided to OPS to convert OPS in cysteine. The enzyme was first found in *Aeropyrum pernix*, *Mycobacterium tuberculosis*, *Mycobacterium smegmatics*, and *Trichomonas vaginalis* (Mino K and Ishikawa K, FEBSletters, 551: 133-138, 2003; Burns K E et al., J. Am. Chem. Soc., 127: 11602-11603, 2005). In addition, the scope of OPSS includes not only wild-type OPSS protein, but also a variant that comprises a deletion, substitution or addition in one or more nucleotides of a polynucleotide sequence encoding the OPSS and shows activity that is equal to or higher than the biological activity of wild-type OPSS protein. Further, the scope of OPSS includes the OPSS protein disclosed in Korean Patent Publication No. 10-2012-0041115 and Korean Patent Registration No. 10-1208267, and its variants.

The sulfide that is used in the present invention may be any sulfide that may be provided not only in a solid form that is generally used in the art, but also in a liquid or gas form due to the difference in pH, pressure and/or solubility, and may be converted to a thiol (SH) group in the form of, for example, sulfide ($S^{2-}$) or thiosulfate ($S_2O_3^{2-}$). Specifically, the sulfide that is used in the present invention may be $Na_2S$, NaSH, $H_2S$, $(NH_4)_2S$, NaSH or $Na_2S_2O_3$, which can provide a thiol group to OPS. In the reaction, a single thiol group is supplied to a single reactive OPS group to produce a single cysteine or a derivative thereof. In this reaction, a sulfide is specifically added in an amount of 0.1-3 moles, and specifically 1-2 moles per mole of OPS. Most specifically, OPS and a sulfide that provides a thiol group are used at a molar ratio of 1:1 in light of economy.

In addition, the method of the present invention further comprises a step of isolating and purifying the cysteine produced by the reaction of step b). Herein, the desired cysteine can be collected by isolating and purifying it from the reaction solution using a suitable reaction known in the art.

Further, the cysteine produced by the method of the present invention can be easily synthesized into a cysteine derivative by a chemical synthesis reaction known in the art.

As used herein, the term "derivatives" refers to similar compounds obtained by chemically modifying a portion of any compound. Usually, the term means compounds in which a hydrogen atom or an atom group substituted with another hydrogen atom or atom group.

As used herein, the term "cysteine derivatives" refers to compounds in which a hydrogen atom or atom group in cysteine is substituted with another atom or atom group. For example, the cysteine derivatives may have a form in which the nitrogen atom of the amine group (—NH$_2$) or the sulfur atom of the thiol group (—SH) in cysteine has another atom or atom group attached thereto. Examples of cysteine derivatives include, but are not limited to, NAC (N-acetylcysteine), SCMC (S-carboxymetylcysteine), BOC—CYS(ME)-OH, (R)—S-(2-amino-2-carboxyethyl)-L-homocysteine, (R)-2-amino-3-sulfopropionic acid, D-2-amino-4-(ethylthio)butyric acid, 3-sulfino-L-alanine, Fmoc-cys(Bocmethyl)-OH, seleno-L-cystine, S-(2-thiazolyl)-L-cysteine, S-(2-thienyl)-L-cysteine, S-(4-tolyl)-L-cysteine, etc. Cysteine can be easily synthesized into NAC (N-acetylcysteine) by reaction with an acetylation agent, and in basic conditions, it can be synthesized into SCMC (S-carboxymetylcysteine) by reaction with haloacetic acid. These cysteine derivatives are used mainly as pharmaceutical materials, including cough remedies, cough-relieving agents, and therapeutic agents for bronchitis, bronchial asthma and sore throat.

Hereinafter, the present invention will be described in further detail with reference to examples. It is to be understood, however, that these examples are for illustrative purposes only and are not intended to limit the scope of the present invention.

Example 1

Identification of Novel Membrane Proteins Having O-Phosphoserine Exporting Activity In order to identify *E. coli* membrane proteins that are involved in the export of O-phosphoserine, screening was performed using the genomic DNA library of *Echerichia coli* K12_W3110 (ATCC 27325).

Specifically, to set up the conditions in which the growth of *E. coli* is inhibited by OPS, a platform strain producing OPS was constructed. The platform strain for screening was a recombinant microorganism mutated to reduce the activity of endogenous phosphoserine phosphatase (SerB) in the wild-type *E. coli* strain W3110 and was named "CA07-0012" (KCCM11212P; Korean Patent Publication No. 10-2012-0041115). Using the OPS-producing strain CA07-0012, optimal screening conditions showing growth inhibition were established by additionally adding OPS to the medium.

Then, the genomic library plasmids of W3110 were transformed into CA07-0012 by electroporation (van der Rest et al. 1999), and colonies showing the removal of growth inhibition under medium conditions containing an excessive amount of OPS were selected. Plasmids were obtained from the selected colonies, and the nucleotide sequences thereof were analyzed by a sequencing technique. As a result, two *E. coli* membrane proteins involved in removing growth inhibition under medium conditions containing an excessive amount of OPS were identified.

The two *E. coli* membrane proteins were identified to be yggT and macB, which encode the predicted inner membrane protein (SEQ ID NO: 1) and the MacAB-TolC macrolide export transport system-membrane subunit (SEQ ID NO: 2), respectively (Ito T, Uozumi N, Nakamura T, Takayama S, Matsuda N, Aiba H, Hemmi H, Yoshimura T (2009). "The implication of YggT of *Escherichia coli* in osmotic regulation." Biosci Biotechnol Biochem 73(12); 2698-704. PMID: 19966467, Pao S S, Paulsen I T, Saier H (1998). "Major facilitator superfamily." Microbiol Mol Biol Rev 1998; 62(1); 1-34. PMID: 9529885).

Example 2

Construction of yggT- and macB-Overexpressing Vectors

In order to examine whether OPS exporting activity is enhanced when the YggT and MacB genes identified in Example 1, which are involved in removing growth inhibition by O-phosphoserine, are enhanced in OPS-producing strains, vectors that express each of the genes were constructed.

Because the present inventors confirmed that the concentration of OPS increased when the homoserine/homoserine lactone transporter RhtB was enhanced in the OPS-producing strain (Korean Patent Publication No. 10-2012-0041115), the RhtB-enhanced strain was used as a positive control in an experiment for examining the productivity of OPS. In addition, the multidrug export transporters EmrD and YcaD MFS belonging to the major facilitator superfamily (MFS), to which MacB belongs, were also evaluated.

In this Example, a fragment of the gene yggT (SEQ ID NO: 3; Accession Number: b3473) encoding YggT (predicted inner membrane protein) and a fragment of the gene macB (SEQ ID NO: 4; Accession Number: b2077) encoding MacB (MacAB-TolC macrolide export transport system-membrane subunit) were obtained by PCR using the genomic DNA of W3110 as a template.

The primer sequences used to construct the vectors expressing each of the *E. coli* membrane proteins are shown in Table 1 below.

TABLE 1

| Genes | Primers (5'→3') | SEQ ID NOS | Vectors |
|---|---|---|---|
| rhtB | GATATCATGACCTTAG AATGGTGG | SEQ ID NO: 9 | pCL-PrhtB-rhtB |
|  | AAGCTTTCACGCATGC CTCGCCGA | SEQ ID NO: 10 |  |
| yggT | GATATCATGAATACGT TGACTTTCCTGCTTTC | SEQ ID NO: 5 | pCL-PrhtB-yggT |
|  | AAGCTTTCATAACGCC ATCCACAGCC | SEQ ID NO: 6 |  |
| macB | GATATCATGACGCCTT TGCTCGAATTA | SEQ ID NO: 7 | pCL-PrhtB-macB |
|  | AAGCTTTTACTCTCGT GCCAGAGCATCT | SEQ ID NO: 8 |  |
| emrD | GATATCATGAAAAGGC AAAGAAACGTCAA | SEQ ID NO: 11 | pCL-PrhtB-emrD |
|  | AAGCTTTTAAACGGGC TGCCCCT | SEQ ID NO: 12 |  |
| ycaD | GATATCATGTCCACGT ATACCCAGCCTG | SEQ ID NO: 13 | pCL-PrhtB-ycaD |
|  | AAGCTTTTACACGTGA GCAACGGGTTT | SEQ ID NO: 14 |  |
| pCL1920 | AAGCTTCGGGCCTCTT CGCTATTACGC | SEQ ID NO: 15 |  |
|  | AAGCTTAGGCTTACCC GTCTTACTGTC | SEQ ID NO: 16 |  |

Specifically, PCR for yggT was performed using the primers of SEQ ID NOS: 5 and 6, and PCR for macB was performed using the primers of SEQ ID NOS: 7 and 8. The primers used in PCR were constructed based on the information of the K12 W3110 gene (GenBank accession number AP 003471) deposited in the NIH GenBank and surrounding nucleotide sequences. Each of the amplified gene fragments was treated with the restriction enzymes EcoRV and HindIII and cloned into the EcoRV and HindIII restriction enzyme sites of a pCL-PrhtB vector comprising the promoter of *E. coli* rhtB gene inserted into a pCL1920 vector (GenBank No AB236930), thereby constructing pCL-PrhtB-yggT, pCL-PrhtB-macB, pCL-PrhtB-emrD, and pCL-PrhtB-ycaD.

In addition, each gene fragment comprising the rhtB promoter was amplified using each of the five constructed plasmids as a template and the primers of SEQ ID NOS: 15 and 16. Each of the amplified fragments was treated with the restriction enzyme Hind and cloned into pCL-Prmf-serA* (G336V)-serC (Korean Patent Publication No. 10-2012-0041115) comprising the serA gene resistant to serine feedback and the serC gene, thereby constructing pCL-Prmf-serA*(G336V)-serC-PrhtB-rhtB, pCL-Prmf-serA*(G336V)-serC-PrhtB-yggT, pCL-Prmf-serA*(G336V)-serC-PrhtB-macB, pCL-Prmf-serA*(G336V)-serC-PrhtB-emrD, and pCL-Prmf-serA*(G336V)-serC-PrhtB-ycaD.

Example 3

Construction of YggT- and MacB-Enhanced Strains and Evaluation of Productivity of O-Phosphoserine Each of the five plasmids constructed in Example 3 was introduced into the OPS-producing strain CA07-0012, and then the O-phosphoserine productivities of the resulting strains were evaluated.

Specifically, each of the strains was plated on LB solid medium and cultured overnight in an incubator at 33° C. Each of the strains cultured overnight on the LB solid medium was inoculated into a 25-mL titer medium shown in Table 2 below, and was then incubated in an cultured at 34.5° C. and 200 rpm for 30 hours. The results of the culture are shown in Table 3.

TABLE 2

| Composition | Concentration (per liter) |
| --- | --- |
| Glucose | 50 g |
| KH$_2$PO$_4$ | 6 g |
| (NH$_4$)$_2$SO$_4$ | 17 g |
| MgSO$_4$•7H$_2$O | 1 g |
| FeSO$_4$•7H$_2$O | 5 mg |
| MnSO$_4$•4H$_2$O | 10 mg |
| L-glycine | 2.5 g |
| Yeast extract | 3 g |
| Calcium carbonate | 30 g |
| pH | 6.8 |

TABLE 3

| Name of strain | OD562 nm | Consumption of glucose (g/L) | O-phosphoserine (g/L) |
| --- | --- | --- | --- |
| CA07-0012 | 35 | 32 | 1.1 |
| CA07-0012/pCL-PrhtB-rhtB | 40 | 35 | 1.3 |
| CA07-0012/pCL-PrhtB-yggT | 37 | 34 | 1.6 |
| CA07-0012/pCL-PrhtB-macB | 41 | 32 | 1.5 |
| CA07-0012/pCL-PrhtB-emrD | 38 | 34 | 1.2 |
| CA07-0012/pCL-PrhtB-ycaD | 37 | 33 | 0.9 |

As can be seen in Table 3 above, when the *E. coli* membrane protein gene yggT or macB was additionally introduced into the *E. coli* CA07-0012 strain, the production of O-phosphoserine in the strain was significantly increased compared to those in the control CA07-0012 and the strains having enhanced rhtB, emrD or ycaD.

In addition, using the OPS-producing strain CA07-0022/pCL-Prmf-serA*(G336V)-serC (KCCM11103P; Korean Patent Publication No. 102012004115) having increased OPS productivity as a result of enhancing the activities of SerA (D-3-phosphoglycerate dehydrogenase) and SerC (3-phosphoserine aminotransferase) that are involved in the biosynthesis pathway of OPS, the increase in OPS productivity by the OPS exporting activity of the *E. coli* membrane proteins YggT and MacB of the present invention was confirmed. The results are shown in Table 4 below.

TABLE 4

| Name of strain | OD562 nm | Consumption of glucose (g/L) | O-phosphoserine (g/L) |
| --- | --- | --- | --- |
| CA07-0022/pCL-Prmf-serA*(G336V)-serC | 30 | 27 | 2.4 |
| CA07-0022/pCL-Prmf-serA*(G336V)-serC-PrhtB-rhtB | 32 | 28 | 2.8 |
| CA07-0022/pCL-Prmf-serA*(G336V)-serC-PrhtB-yggT | 28 | 26 | 3.0 |
| CA07-0022/pCL-Prmf-serA*(G336V)-serC-PrhtB-macB | 27 | 27 | 2.8 |
| CA07-0022/pCL-Prmf-serA*(G336V)-serC-PrhtB-emrD | 33 | 29 | 2.3 |
| CA07-0022/pCL-Prmf-serA*(G336V)-serC-PrhtB-ycaD | 34 | 28 | 1.9 |

As can be seen in Table 4 above, when the *E. coli* membrane protein was additionally introduced into CA07-0022/pCL-Prmf-serA*(G336V)-serC having enhanced OPS productivity compared to the *E. coli* CA07-0012 strain, the production of OPS in the strain having enhanced activity of the yggT or macB protein gene increased by about 120% compared to that in the control strain, similar to the results shown in Table 3 above, whereas the production of OPS in the comparative strain having enhanced emrD or ycaD decreased compared to that in the control strain.

In addition, CA07-0022/pCL-Prmf-serA*(G336V)-serC-PrhtB-yggT that is a representative example of the OPS-producing microorganism having enhanced activity of YggT of SEQ ID NO: 1 was named "*Escherichia coli* CA07-0228" and deposited with the Korean Culture Center of Microorganisms, recognized as an international depositary authority under the Budapest Treaty, on Mar. 7, 2013 under the accession number KCCM11399P. Also, CA07-0022/pCL-Prmf-serA*(G336V)-serC-PrhtB-macB that is a representative example of the OPS-producing strain having enhanced activity of MacB of SEQ ID NO: 2 was named "*Escherichia coli* CA07-0229" and deposited with the Korean Culture Center of Microorganisms, recognized as an international depositary authority under the Budapest Treaty, on Mar. 7, 2013 under the accession number KCCM11400P.

The above-described results indicate that the YggT and MacB proteins of the present invention have excellent OPS exporting activities, unlike other proteins belonging to the same family, suggesting that the proteins of the present invention are useful for the production of OPS.

Example 4

Examination of Functions of YggT and MacB

Among the samples confirmed to produce OPS in Example 3, the negative control sample having no enhanced membrane protein and the samples having enhanced YggT or MacB proteins were used. Specifically, OPS exported into the medium was completely removed, and then only the cells were collected and disrupted. Then, the concentration of OPS in the cells was measured using an HPLC instrument, and the results of the measurement are shown in FIG. 1.

As a result, it was shown that the intracellular OPS concentration of the strains having enhanced YggT or MacB was reduced by 30% compared to that of the control. Such results suggest that yggT and macB function to export OPS from cells, indicating that, when yggT or macB is enhanced in an OPS-producing strain, it can function to export OPS from the cells of the strain, thereby increasing the production of OPS (FIG.

As described above, the inventive novel polypeptide having the amino acid sequence of SEQ ID NO: 1 or 2 has excellent OPS exporting activity, and thus when the polypeptide is applied to an O-phosphoserine-producing microorganism, O-phosphoserine can be produced with high efficiency in the microorganism.

Although the preferred embodiments of the present invention have been described for illustrative purposes, those skilled in the art will appreciate that various modifications, additions and substitutions are possible, without departing from the scope and spirit of the invention as disclosed in the accompanying claims.

What is claimed is:

1. A method for producing O-phosphoserine (OPS), comprising culturing an O-phosphoserine-producing microorganism having enhanced activity of a polypeptide that has the amino acid sequence of SEQ ID NO: 1 or 2 having O-phosphoserine exporting activity, compared to the activity of the polypeptide of a wild-type microorganism,
wherein the O-phosphoserine-producing microorganism further has reduced activity of endogenous phosphoserine phosphatase.

2. The method according to claim 1, wherein the O-phosphoserine-producing microorganism further has enhanced activity of phosphoglycerate dehydrogenase or phosphoserine aminotransferase.

3. An O-phosphoserine-producing microorganism having enhanced activity of a polypeptide that has the amino acid sequence of SEQ ID NO: 1 or 2 having O-phosphoserine exporting activity, compared to the activity of the polypeptide of a wild-type microorganism,
wherein the microorganism further has reduced activity of endogenous phosphoserine phosphatase.

4. The microorganism according to claim 3, wherein the microorganism further has enhanced activity of phosphoglycerate dehydrogenase or phosphoserine aminotransferase.

5. A method for producing cysteine or its derivatives, comprising the steps of:
a) culturing the microorganism of claim 3 to produce O-phosphoserine (OPS); and
b) reacting the O-phosphoserine, produced in step a), with a sulfide in the presence of O-phosphoserine sulfhydrylase (OPSS) or a microorganism that expresses OPSS.

6. The method according to claim 5, wherein the sulfide is one or more selected from the group consisting of $Na_2S$, NaSH, $(NH_4)_2S$, $H_2S$ and $Na_2S_2O_3$.

7. A method for producing cysteine or its derivatives, comprising the steps of:
a) culturing the microorganism of claim 4 to produce O-phosphoserine (OPS); and
b) reacting the O-phosphoserine, produced in step a), with a sulfide in the presence of O-phosphoserine sulfhydrylase (OPSS) or a microorganism that expresses OPSS.

8. The method according to claim 7, wherein the sulfide is one or more selected from the group consisting of $Na_2S$, NaSH, $(NH_4)_2S$, $H_2S$ and $Na_2S_2O_3$.

* * * * *

SEQUENCE LISTING

```
<160> NUMBER OF SEQ ID NOS: 16

<210> SEQ ID NO 1
<211> LENGTH: 188
<212> TYPE: PRT
<213> ORGANISM: Escherichia coli
<220> FEATURE:
<221> NAME/KEY: PEPTIDE
<222> LOCATION: (1)..(88)
<223> OTHER INFORMATION: Predicted inner membrane protein, YggT

<400> SEQUENCE: 1

Met Asn Thr Leu Thr Phe Leu Leu Ser Thr Val Ile Glu Leu Tyr Thr
1               5                   10                  15

Met Val Leu Leu Leu Arg Ile Trp Met Gln Trp Ala His Cys Asp Phe
                20                  25                  30

Tyr Asn Pro Phe Ser Gln Phe Val Val Lys Val Thr Gln Pro Ile Ile
            35                  40                  45

Gly Pro Leu Arg Arg Val Ile Pro Ala Met Gly Pro Ile Asp Ser Ala
        50                  55                  60

Ser Leu Leu Val Ala Tyr Ile Leu Ser Phe Ile Lys Ala Ile Val Leu
65                  70                  75                  80

Phe Lys Val Val Thr Phe Leu Pro Ile Ile Trp Ile Ala Gly Leu Leu
                85                  90                  95

Ile Leu Leu Lys Thr Ile Gly Leu Leu Ile Phe Trp Val Leu Leu Val
                100                 105                 110

Met Ala Ile Met Ser Trp Val Ser Gln Gly Arg Ser Pro Ile Glu Tyr
            115                 120                 125

Val Leu Ile Gln Leu Ala Asp Pro Leu Leu Arg Pro Ile Arg Arg Leu
        130                 135                 140

Leu Pro Ala Met Gly Gly Ile Asp Phe Ser Pro Met Ile Leu Val Leu
145                 150                 155                 160

Leu Leu Tyr Val Ile Asn Met Gly Val Ala Glu Val Leu Gln Ala Thr
                165                 170                 175

Gly Asn Met Leu Leu Pro Gly Leu Trp Met Ala Leu
                180                 185

<210> SEQ ID NO 2
<211> LENGTH: 648
<212> TYPE: PRT
<213> ORGANISM: Escherichia coli
<220> FEATURE:
<221> NAME/KEY: PEPTIDE
<222> LOCATION: (1)..(648)
<223> OTHER INFORMATION: MacAB-TolC macrolide efflux transport
      system - membrane subunit (MacB)

<400> SEQUENCE: 2
```

```
Met Thr Pro Leu Leu Glu Leu Lys Asp Ile Arg Arg Ser Tyr Pro Ala
1               5                   10                  15

Gly Asp Glu Gln Val Glu Val Leu Lys Gly Ile Ser Leu Asp Ile Tyr
            20                  25                  30

Ala Gly Glu Met Val Ala Ile Val Gly Ala Ser Gly Ser Gly Lys Ser
            35                  40                  45

Thr Leu Met Asn Ile Leu Gly Cys Leu Asp Lys Ala Thr Ser Gly Thr
50                      55                  60

Tyr Arg Val Ala Gly Gln Asp Val Ala Thr Leu Asp Ala Asp Ala Leu
65                  70                  75                  80

Ala Gln Leu Arg Arg Glu His Phe Gly Phe Ile Phe Gln Arg Tyr His
            85                  90                  95

Leu Leu Ser His Leu Thr Ala Glu Gln Asn Val Glu Val Pro Ala Val
            100                 105                 110

Tyr Ala Gly Leu Glu Arg Lys Gln Arg Leu Leu Arg Ala Gln Glu Leu
            115                 120                 125

Leu Gln Arg Leu Gly Leu Glu Asp Arg Thr Glu Tyr Tyr Pro Ala Gln
            130                 135                 140

Leu Ser Gly Gly Gln Gln Arg Val Ser Ile Ala Arg Ala Leu Met
145                 150                 155                 160

Asn Gly Gly Gln Val Ile Leu Ala Asp Glu Pro Thr Gly Ala Leu Asp
                165                 170                 175

Ser His Ser Gly Glu Glu Val Met Ala Ile Leu His Gln Leu Arg Asp
            180                 185                 190

Arg Gly His Thr Val Ile Val Thr His Asp Pro Gln Val Ala Ala
            195                 200                 205

Gln Ala Glu Arg Val Ile Glu Ile Arg Asp Gly Glu Ile Val Arg Asn
            210                 215                 220

Pro Pro Ala Ile Glu Lys Val Asn Val Thr Gly Gly Thr Glu Pro Val
225                 230                 235                 240

Val Asn Thr Val Ser Gly Trp Arg Gln Phe Val Ser Gly Phe Asn Glu
                245                 250                 255

Ala Leu Thr Met Ala Trp Arg Ala Leu Ala Ala Asn Lys Met Arg Thr
            260                 265                 270

Leu Leu Thr Met Leu Gly Ile Ile Gly Ile Ala Ser Val Val Ser
            275                 280                 285

Ile Val Val Gly Asp Ala Ala Lys Gln Met Val Leu Ala Asp Ile
            290                 295                 300

Arg Ser Ile Gly Thr Asn Thr Ile Asp Val Tyr Pro Gly Lys Asp Phe
305                 310                 315                 320

Gly Asp Asp Pro Gln Tyr Gln Gln Ala Leu Lys Tyr Asp Asp Leu
            325                 330                 335

Ile Ala Ile Gln Lys Gln Pro Trp Val Ala Ser Ala Thr Pro Ala Val
            340                 345                 350

Ser Gln Asn Leu Arg Leu Arg Tyr Asn Val Asp Val Ala Ala Ser
            355                 360                 365

Ala Asn Gly Val Ser Gly Asp Tyr Phe Asn Val Tyr Gly Met Thr Phe
            370                 375                 380

Ser Glu Gly Asn Thr Phe Asn Gln Glu Gln Leu Asn Gly Arg Ala Gln
385                 390                 395                 400

Val Val Val Leu Asp Ser Asn Thr Arg Arg Gln Leu Phe Pro His Lys
                405                 410                 415

Ala Asp Val Val Gly Glu Val Ile Leu Val Gly Asn Met Pro Ala Arg
```

```
                420             425             430
Val Ile Gly Val Ala Glu Glu Lys Gln Ser Met Phe Gly Ser Ser Lys
            435                 440                 445
Val Leu Arg Val Trp Leu Pro Tyr Ser Thr Met Ser Gly Arg Val Met
        450                 455                 460
Gly Gln Ser Trp Leu Asn Ser Ile Thr Val Arg Val Lys Glu Gly Phe
465                 470                 475                 480
Asp Ser Ala Glu Ala Glu Gln Gln Leu Thr Arg Leu Leu Ser Leu Arg
                485                 490                 495
His Gly Lys Lys Asp Phe Phe Thr Trp Asn Met Asp Gly Val Leu Lys
            500                 505                 510
Thr Val Glu Lys Thr Thr Arg Thr Leu Gln Leu Phe Leu Thr Leu Val
        515                 520                 525
Ala Val Ile Ser Leu Val Val Gly Gly Ile Gly Val Met Asn Ile Met
            530                 535                 540
Leu Val Ser Val Thr Glu Arg Thr Arg Glu Ile Gly Ile Arg Met Ala
545                 550                 555                 560
Val Gly Ala Arg Ala Ser Asp Val Leu Gln Gln Phe Leu Ile Glu Ala
                565                 570                 575
Val Leu Val Cys Leu Val Gly Gly Ala Leu Gly Ile Thr Leu Ser Leu
            580                 585                 590
Leu Ile Ala Phe Thr Leu Gln Leu Phe Leu Pro Gly Trp Glu Ile Gly
            595                 600                 605
Phe Ser Pro Leu Ala Leu Leu Leu Ala Phe Leu Cys Ser Thr Val Thr
        610                 615                 620
Gly Ile Leu Phe Gly Trp Leu Pro Ala Arg Asn Ala Ala Arg Leu Asp
625                 630                 635                 640
Pro Val Asp Ala Leu Ala Arg Glu
            645

<210> SEQ ID NO 3
<211> LENGTH: 567
<212> TYPE: DNA
<213> ORGANISM: Escherichia coli
<220> FEATURE:
<221> NAME/KEY: gene
<222> LOCATION: (1)..(567)
<223> OTHER INFORMATION: yggT

<400> SEQUENCE: 3
atgaatacgt tgactttcct gctttcaacg gtcattgagc tgtataccat ggtgctgtta      60
ttacgcatct ggatgcagtg gctcattgt gatttttaca accccttctc acagtttgta     120
gtgaaggtaa cgcagccaat tatcgggcca ctgcgccgcg ttattccggc aatggggcca     180
attgacagcg cctcgctgct ggttgcctat attctcagtt ttatcaaagc catcgtgctg     240
tttaaagtgg tgaccttcct gccaatcatc tggattgccg gtttactgat tctgctgaaa     300
accatcggcc tgctgatttt ctgggtcctg ctggtgatgg cgattatgag ctgggtaagc     360
caggggcgta gcccgattga atacgtgctg attcagctgg ccgatccgct gctgcgcccg     420
attcgccgcc tgctaccggc aatggtggg attgatttct cgccgatgat cctcgttctg     480
ctgctgtatg tcatcaatat gggtgtcgca gaagtattac aggcaaccgg aaatatgctg     540
ctgccagggc tgtggatggc gttatga                                          567

<210> SEQ ID NO 4
<211> LENGTH: 1947
```

<212> TYPE: DNA
<213> ORGANISM: Escherichia coli
<220> FEATURE:
<221> NAME/KEY: gene
<222> LOCATION: (1)..(1947)
<223> OTHER INFORMATION: macB

<400> SEQUENCE: 4

| | | | | | |
|---|---|---|---|---|---|
| atgacgcctt | tgctcgaatt | aaaggatatt | cgtcgcagct | atcctgccgg | tgatgagcag | 60 |
| gttgaggtgc | tgaagggcat | cagcctcgat | atttatgcgg | gtgagatggt | cgcgattgtt | 120 |
| ggcgcttcgg | gttccggtaa | atcgaccctg | atgaatattc | tcggctgtct | ggataaggcc | 180 |
| accagcggca | cctatcgcgt | cgccggtcag | gatgttgcca | cgctggacgc | cgatgcgctg | 240 |
| gcgcaactgc | gccgcgagca | tttcggcttt | attttccagc | gttaccattt | gctttcgcat | 300 |
| ttaaccgccg | agcagaacgt | tgaagtaccc | gccgtctatg | ctggtcttga | gcggaaacag | 360 |
| cgactgcttc | gtgcccagga | gttgctgcaa | cggctggggc | tggaagaccg | tacagagtat | 420 |
| tatccggcac | agctttcggg | tggtcagcaa | cagcgcgtca | gcatcgcgcg | ggcattgatg | 480 |
| aacggtggtc | aggtaattct | tgccgatgaa | ccaaccggcg | cactggacag | ccattctggc | 540 |
| gaagaggtga | tggcgatcct | gcatcagctg | cgcgatcgtg | gcatacggt | gattatcgtc | 600 |
| acccacgatc | cgcaggtcgc | tgctcaggcc | gagcgggtga | tcgaaattcg | cgacggcgaa | 660 |
| attgtgcgca | atcctcccgc | cattgaaaaa | gtgaatgtta | ctggcgggac | ggaacctgtt | 720 |
| gtcaacacgg | tgtctggctg | gcggcagttt | gtcagcggtt | ttaacgaggc | gctgacgatg | 780 |
| gcatggcggg | cgctggcagc | gaataaaatg | cgtactttac | tgaccatgct | ggggattatt | 840 |
| atcggtattg | cgtcggtggt | ttccattgtc | gtggtgggtg | acgccgccaa | acaaatggtg | 900 |
| ctggcggata | ttcgttctat | tggtacgaat | actattgatg | tctatcccgg | aaagatttt | 960 |
| ggcgatgacg | atccgcaata | tcagcaggcg | ctgaagtacg | acgacttaat | cgccatccaa | 1020 |
| aaacaaccgt | gggtcgcctc | agccacacct | gccgtctcgc | aaaacctgcg | cctgcgttat | 1080 |
| aacaatgttg | atgttgctgc | cagtgccaat | ggcgtgagcg | gcgattattt | taatgtctat | 1140 |
| ggcatgacct | tcagtgaagg | aaacaccttt | aatcaggagc | agctgaacgg | tcgtgcgcag | 1200 |
| gtcgtggttc | tcgacagtaa | tactcgccgc | cagcttttcc | cccataaagc | agatgtggtt | 1260 |
| ggcgaggtga | ttctggtcgg | caatatgccc | gccagagtca | ttggtgtggc | ggaagaaaaa | 1320 |
| cagtcgatgt | ttggtagcag | taaagtgctg | cgtgtctggc | taccttacag | cacgatgtcc | 1380 |
| gggcgagtta | tgggccagtc | gtggcttaac | tccattactg | tcagggtgaa | agaaggattt | 1440 |
| gacagcgccg | aggcggaaca | gcaactcacg | cgtttacttt | cactgcgcca | cggaaagaag | 1500 |
| gatttcttta | cctggaacat | ggacggcgtc | ttgaaaactg | ttgaaaagac | cacacgtact | 1560 |
| ttacaactgt | ttctgacgct | ggtggcggtg | atttcgctgg | tggtgggcgg | tattggtgta | 1620 |
| atgaatatta | tgctggtgtc | agtgaccgag | cggacgcggg | aaattggcat | tcgcatggct | 1680 |
| gtaggtgcgc | gagcaagcga | tgttttgcaa | cagttcctga | tcgaagccgt | actggtttgc | 1740 |
| ctggtcggtg | gcgcgttggg | aataacactg | tcactgttaa | ttgctttcac | cttgcagctt | 1800 |
| ttcttacccg | gctgggagat | tggttttca | ccgttggcgc | tgctgctggc | gtttctctgc | 1860 |
| tcgacggtca | ccgggatttt | atttggctgg | ttacccgcac | gaaatgcggc | acgactggat | 1920 |
| ccagtagatg | ctctggcacg | agagtaa | | | | 1947 |

<210> SEQ ID NO 5
<211> LENGTH: 32
<212> TYPE: DNA

```
<213> ORGANISM: Artificial Sequence
<220> FEATURE:
<223> OTHER INFORMATION: primer for amplification of yggT to construct
      pCL-PrhtB-yggT

<400> SEQUENCE: 5
gatatcatga atacgttgac tttcctgctt tc                                   32

<210> SEQ ID NO 6
<211> LENGTH: 26
<212> TYPE: DNA
<213> ORGANISM: Artificial Sequence
<220> FEATURE:
<223> OTHER INFORMATION: primer for amplification of yggT to construct
      pCL-PrhtB-yggT

<400> SEQUENCE: 6
aagctttcat aacgccatcc acagcc                                          26

<210> SEQ ID NO 7
<211> LENGTH: 27
<212> TYPE: DNA
<213> ORGANISM: Artificial Sequence
<220> FEATURE:
<223> OTHER INFORMATION: primer for amplification of macB to construct
      pCL-PrhtB-macB

<400> SEQUENCE: 7
gatatcatga cgcctttgct cgaatta                                         27

<210> SEQ ID NO 8
<211> LENGTH: 28
<212> TYPE: DNA
<213> ORGANISM: Artificial Sequence
<220> FEATURE:
<223> OTHER INFORMATION: primer for amplification of macB to construct
      pCL-PrhtB-macB

<400> SEQUENCE: 8
aagcttttac tctcgtgcca gagcatct                                        28

<210> SEQ ID NO 9
<211> LENGTH: 24
<212> TYPE: DNA
<213> ORGANISM: Artificial Sequence
<220> FEATURE:
<223> OTHER INFORMATION: primer for amplification of rhtB to construct
      pCL-PrhtB-rhtB

<400> SEQUENCE: 9
gatatcatga ccttagaatg gtgg                                            24

<210> SEQ ID NO 10
<211> LENGTH: 24
<212> TYPE: DNA
<213> ORGANISM: Artificial Sequence
<220> FEATURE:
<223> OTHER INFORMATION: primer for amplification of rhtB to construct
      pCL-PrhtB-rhtB

<400> SEQUENCE: 10
aagctttcac gcatgcctcg ccga                                            24

<210> SEQ ID NO 11
<211> LENGTH: 29
<212> TYPE: DNA
<213> ORGANISM: Artificial Sequence
```

```
<220> FEATURE:
<223> OTHER INFORMATION: primer for amplification of emrD to construct
      pCL-PrhtB-emrD

<400> SEQUENCE: 11
gatatcatga aaaggcaaag aaacgtcaa                                           29

<210> SEQ ID NO 12
<211> LENGTH: 23
<212> TYPE: DNA
<213> ORGANISM: Artificial Sequence
<220> FEATURE:
<223> OTHER INFORMATION: primer for amplification of emrD to construct
      pCL-PrhtB-emrD

<400> SEQUENCE: 12
aagcttttaa acgggctgcc cct                                                 23

<210> SEQ ID NO 13
<211> LENGTH: 28
<212> TYPE: DNA
<213> ORGANISM: Artificial Sequence
<220> FEATURE:
<223> OTHER INFORMATION: primer for amplification of ycaD to construct
      pCL-PrhtB-ycaD

<400> SEQUENCE: 13
gatatcatgt ccacgtatac ccagcctg                                            28

<210> SEQ ID NO 14
<211> LENGTH: 27
<212> TYPE: DNA
<213> ORGANISM: Artificial Sequence
<220> FEATURE:
<223> OTHER INFORMATION: primer for amplification of ycaD to construct
      pCL-PrhtB-ycaD

<400> SEQUENCE: 14
aagcttttac acgtgagcaa cgggttt                                             27

<210> SEQ ID NO 15
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      construct pCL-Prmf-serA(G336V)-serC_PrhtB-genes

<400> SEQUENCE: 15
aagcttcggg cctcttcgct attacgc                                             27

<210> SEQ ID NO 16
<211> LENGTH: 27
<212> TYPE: DNA
<213> ORGANISM: Artificial Sequence
<220> FEATURE:
<223> OTHER INFORMATION: primer for amplification of pCL-PrhtB-genes to
      construct pCL-Prmf-serA(G336V)-serC_PrhtB-genes

<400> SEQUENCE: 16
aagcttaggc ttacccgtct tactgtc                                             27
```